USP005104506A

United States Patent [19]

Jones et al.

[11] Patent Number: 5,104,506
[45] Date of Patent: Apr. 14, 1992

[54] METHOD FOR SEPARATING IONIC SPECIES USING CAPILLARY ELECTROPHORESIS

[75] Inventors: William R. Jones, Blackstone; Petr Jandik, Framingham; Michael Merion, Upton, all of Mass.

[73] Assignee: Millipore Corporation, Bedford, Mass.

[21] Appl. No.: 471,535

[22] Filed: Jan. 29, 1990

[51] Int. Cl.$^5$ .................. B01D 57/02; B01D 61/42; G01N 21/00
[52] U.S. Cl. .................. 204/180.1; 356/344; 356/412
[58] Field of Search .................. 204/299 R, 180.1; 356/344, 412

[56] References Cited

U.S. PATENT DOCUMENTS 4,414,842  11/1983  Small et al. .................. 73/61.1 C

OTHER PUBLICATIONS

Foret, J. Chrom., 470:299–308 (1989).
Altria, Chromatography, 24:527–532 (1987).
Huang, Anal., Chem., 61:766–770 (1989).

Primary Examiner—John Niebling
Assistant Examiner—Caroline Koestner
Attorney, Agent, or Firm—Hamilton, Brook, Smith & Reynolds

[57] ABSTRACT

A technique for separating, identifying and measuring ions in solution by capillary zone electrophoresis is described, which provides improved sensitivity and resolution of anionic species. The method involves subjecting a sample containing the ionic species a light-absorbing material and a quaternary ammonium salt to an electrical current in a capillary column causing the ions to elute according to their ionic mobility. The ionic species are detected and quantitated by UV/Visible photometric monitoring.

11 Claims, 2 Drawing Sheets

METHOD FOR SEPARATING IONIC SPECIES USING CAPILLARY ELECTROPHORESIS

BACKGROUND

The separation and/or detection of ionic species is generally carried out by utilizing electrochemical properties of analytes, such as ionic interactions and conductivity in ion chromatography or ionic mobility in capillary electrophoresis. Ion chromatography (IC) is capable of detecting simultaneously a large variety of ionic species at low concentration levels. The ability to separate and detect several ionic species simultaneously is a unique characteristic of IC. However, there are important limitations to IC, including lack of sufficient selectivity for certain types of mixtures, low separation efficiency and a relative complexity of instrumentation.

Capillary electrophoresis (CE) is an efficient analytical separation technique for analysis of minute amounts of sample CE separations are performed in a narrow diameter capillary tube, which is filled with an electrically conductive medium termed the "carrier electrolyte". A current is applied to the carrier electrolyte, and ionic species in the sample move from one electrode toward the other at a rate which is dependent upon certain characteristics, such as molecular charge, size and/or mobility CE may be performed using gels or liquids, such as buffers, in the capillary. In the liquid mode, known as free zone electrophoresis, separations are based on the ratio of charge to Stoke's radius.

CE has several advantages over IC and conventional gel electrophoresis for the separation of ionic species. These include faster separation speed, improved resolution and smaller sample size. For example, separation speeds using CE can be 10 to 20 times faster than conventional gel electrophoresis, and no post-run staining is necessary. In part, high resolution can be obtained through the use of high voltages because of the rapid dissipation of heat by the capillary. Further, band broadening is minimized due to the narrow capillary diameter. In free-zone electrophoresis, the phenomenon of electroosmosis, or electroosmotic flow (EOF), which is the bulk flow of liquid rapidly moves all of the sample molecules whether they are positively charged, negatively charged or neutral. Under certain conditions EOF can contribute to improved resolution and separation speed in free-zone CE.

The detection of some ionic species by CE is problematical, however, due to the "transparency" of many ionic species to light. These ions do not absorb light, so they cannot be detected by conventional photometric means, e g., direct photometric or fluorescent detection. However, these ions can be detected using indirect photometric detection. Indirect photometric detection relies upon the presence of a light absorbing electrolyte ion in the background electrolyte. Non-absorbing species are detected as zones of decreased absorbance or voids in the background due to the displacement of the light absorbing electrolyte ion. Indirect photometric detection has been described using fluorescent, ultraviolet (UV) and UV-visible (UV-vis) absorbing ions in the background electrolyte. For example, Small et al. in U.S. Pat. No. 4,414,842 describe a technique for detecting ions in an ion exchange chromatography system by indirect UV detection in which a UV-absorbing ion is included in the elution buffer. Other methods utilizing indirect photometric detection in chromatography have been described by Foret et al., *J. Chromatography,* 470:299–308 (1989); Kuhr et al., *Anal. Chem.,* 60:2642–2646 (1988); Kuhr et al., *Anal. Chem.,* 60:1832–1834; and Takeuchi et al., *Chromatographia,* 25:1072–1074 (1988). The need exists for a method for separating and detecting ionic molecules which is faster, more efficient, has better resolution, and requires less sample preparation than the available methods.

SUMMARY OF THE INVENTION

The present invention relates to a method for separating and detecting ions by CE using carrier electrolyte solutions which facilitate detection by indirect methods, particularly UV/visible spectroscopy. The present method relies upon a unique combination of reagents which can simultaneously effect a sensitive, high resolution separation of several ionic species ranging from simple inorganic ions to complex organic ions. The method is particularly useful for separating and detecting anions.

The method involves introducing a sample containing the ions into a CE system which utilizes a mixture of reagents which controls the direction of the electroosmatic flow of the carrier electrolyte, and which provides a light-absorbing background at a wavelength suitable for sensitive and interference-free indirect photometric detection of all ionic species. The reagent mixture consists of the salt of a UV-absorbing anion (e.g., iodide, tungstate, molybdate, chromate, ferrocyanide, ferricyanide or benzoate). In addition an alkyl quaternary ammonium salt with at least four carbon atoms in a linear or branched configuration is required. Sodium chromate is a particularly preferred UV-absorbing salt and tetradecyltrimethylammonium bromide (TTAB) or cetyltrimethylammonium bromide (CTAB) are particularly preferred quaternary ammonium salts. Alternatively, the carrier electrolyte can contain only the salt of a UV-absorbing anion while the quaternary ammonium groups are bound (chemically or by absorptive forces) to the capillary wall. The sample is injected into a capillary filled with the reagent mixture, an electric current is applied to the capillary under conditions appropriate to cause the ions in the mixture to move toward the opposite electrode and the ionic species are detected photometrically.

A reagent composition which facilitates the separation and detection by indirect photometric methods is the subject of the present invention. The reagent mixture contains a light absorbing ion which is specific for the UV/visible range and a quaternary ammonium salt. A preferred composition contains a chromate salt and/or benzoate salt with tetradecyltrimethylammonium bromide.

The chemistry necessary to perform CE separations of ionic species for indirect detection can be contained in a kit. Such a kit would contain, inter alia, one or more light absorbing ions specific for the UV/visible range, such as a chromate and/or benzoate salt, and a quaternary ammonium compound.

The present method has several advantages, such as improved sensitivity, the ability to separate and resolve a wide range of ionic species, the ability to detect ionic species which are not detectable by direct methods, less sample preparation and faster separation. The method can be used to separate and detect both simple and complex anions or cations, and to detect a variety of analytes simultaneously.

DETAILED DESCRIPTION OF THE INVENTION

Figure 1:
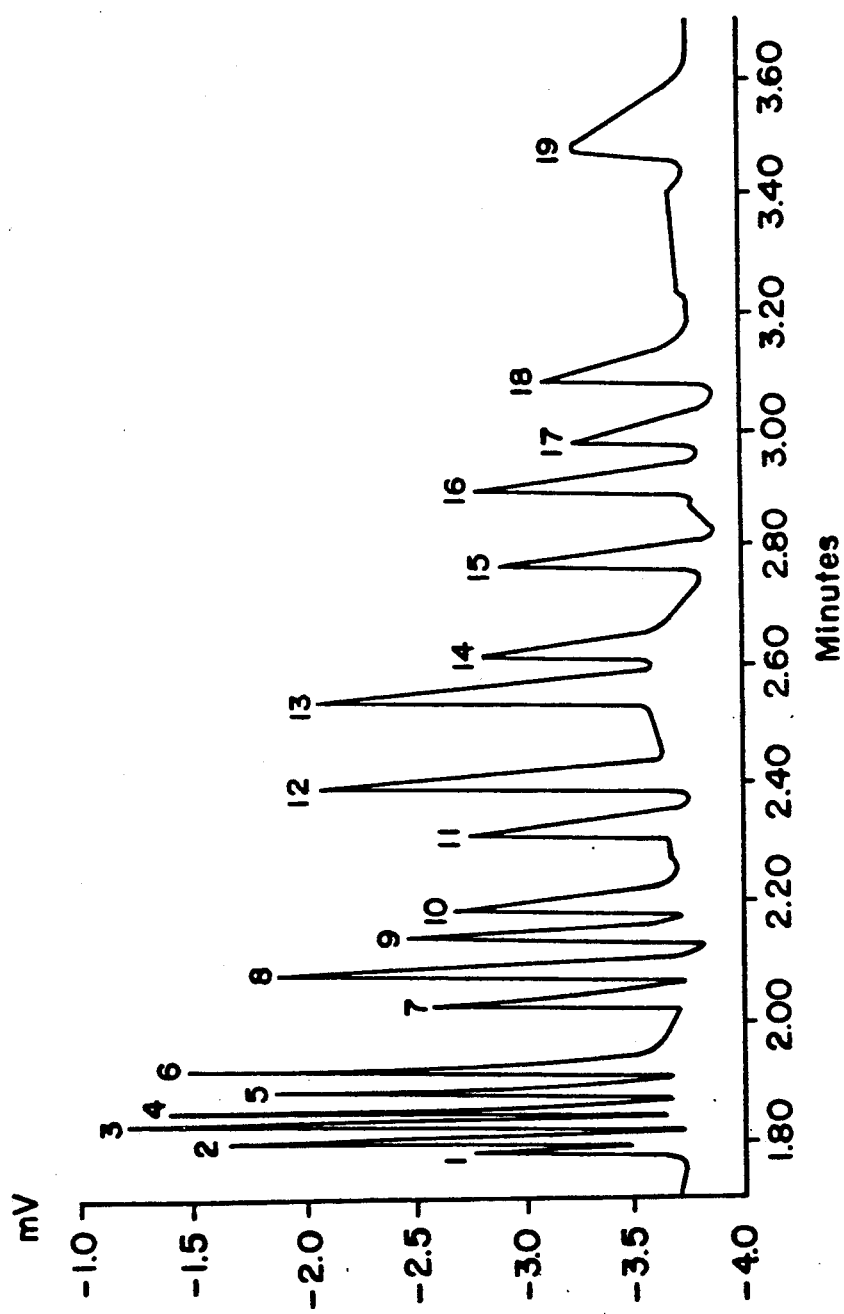
FIG. 1 is a chromatogram showing the separation of nineteen anions by CE using TTAB/Na₂CrO₄ the carrier electrolyte.

The present method utilizes CE to simultaneously separate and detect ionic species contained in a sample using indirect UV/visible detection. Indirect UV/visible spectroscopy is used because many ionic species cannot be detected using direct detection methods CE is a well known technology, and has been described in detail, for example, by Compton and Brownlee in *Biotechniques*, 6(5):432–440 (1988); and Jorgenson and Lukacs in *Science*, 22:266–272 (1983). A method of utilizing indirect photometric detection in CE is described by Foret et al. in *J. Chromatography*, 470:299–308 (1989).

In the present method, a capillary tube is filled with an electrically conductive liquid containing a combination of reagents which facilitate detection by UV/visible spectroscopy. A preferred capillary is generally a fused silica capillary having an internal diameter of about 50 to 100 microns ($\mu$). A preferred combination of reagents includes a chromate or benzoate salt and a quaternary ammonium salt.

The ionic sample is introduced into the capillary, for example, by hydrostatic pressure, vacuum or by electrokinetic injection in which the liquid sample is moved into the capillary by an electric current. After introduction of the sample, each end of the capillary is immersed in a reservoir which contains an electrode and the electrolyte solution containing the reagent mixture (i.e., chromate and/or benzoate salt and quaternary ammonium salt). The capillary tube is positioned with a detector on the column near the end opposite to sample introduction. Electric current is applied and the electrophoretic separation is monitored by indirect UV/visible spectroscopy. Other indirect detection methods can be used, however, UV/visible spectroscopy is preferred because it allows, sensitive rapid detection of ionic species and is less costly than laser detection, for example.

The method relies upon a combination of reagents which facilitates detection by indirect UV/visible spectroscopy, comprising a light-absorbing compound specific for the UV/visible range and one or more quaternary ammonium salts. UV/visible light-absorbing compounds which can be used are absorbing anions, such as iodide, tungstate, molybdate, chromate, ferrocyanide, ferrocyanate and benzoate. Absorbing anions which are particularly useful are selected chromate and benzoate salts. A preferred chromate salt is sodium chromate having a concentration of from about 1 mM to about 20 mM. A preferred concentration of the benzoate salt is (e.g., sodium benzoate) from 10 mM to about 30 mM. Quaternary ammonium salts which can be used contain alkyl groups having at least four carbon atoms in a linear or branched configuration. These quaternary ammonium salts are particularly important to the present technique. Their use facilitates control of both the direction, as well as the rate of electroosmotic flow. Control of this parameter permits the development of an assay that is both high in resolution and is complete in a short period of time. Preferred quaternary ammonium salts are tetradecyltrimethylammoniumbromide (TTAB) and/or cetyltrimethylammonium bromide (CTAB) having a concentration of from about 0.1 mM to about 1.5 mM. The electrolyte solution generally has a pH of from about 7.5 to about 8.5. An acid, such as sulfuric acid or chromic acid, can be added to the electrolyte solution to adjust the pH to the desired level.

The present method can be utilized to analyze most types of ionic species; however, the method is particularly useful for the separation and detection of anions. Samples containing complex mixtures of ions, including anions, cations and organic compounds, for example can be analyzed using the method. When a sample containing such a complex mixture is separated using the present method and electrolyte carrier, the cations in the sample will move away from the detector, and the organic species will move very slowly, thereby creating a window for the anionic species. The anions move most rapidly toward the detector, thus are most efficiently resolved. The method is also useful to analyze samples containing multiple ionic species in the shortest time possible, or to scan an unknown sample for ionic compounds, since the method and reagent mixture can efficiently separate and resolve such mixtures. Samples which can be analyzed using the present method include water, foods, such as juices or ionic organic reaction mixtures.

In one embodiment of the present method, a sample containing eight common inorganic anions: bromide, chloride, nitrate, nitrite, sulfate, fluoride, phosphate and carbonate, was analyzed by CE using a mixture of 0.5 mM TTAB and 5 mM sodium chromate ($Na_2CrO_4$) having a pH of 8 as the carrier electrolyte. All eight anions were detected by monitoring the absorbance of the carrier electrolyte at 254 or 272 nm. Separation of all eight anions was completed in about three minutes. The ionic species were separated based on their ionic mobilities. This is important because the elution sequence using the present method is predictable based on the known ion mobilities of various ions. This means that the chemical identity of an unknown analyte can be reliably determined from its position in the elution order.

Separation of ionic species using the present method is superior to ion chromatographic separations of similar mixtures in at least four respects: improved separation efficiency, shorter runtime, better selectivity and improved sensitivity. For example, the number of theoretical plates for sulfate in the illustrative example used above is 157,344. The highest plate-counts attainable by ion chromatography are smaller than 10,000. Separation of the standard eight anions was completed in three minutes by the present method, whereas ion chromatographic separations of identical mixtures take typically six to fifteen minutes. Injection volumes for the CE separation are less than about 40 nanoliters (nl) compared to about 50 to 100 microliters ($\mu$l) for IC. Even though only 20 nL were injected to obtain the above separation, detection limits for all separated anions were either comparable or better than those observed in IC. This corresponds to a 10,000 fold increase in absolute sensitivity (per $\mu$g injected) in the present CE system in comparison with IC.

The present method provides ionic separations which are efficient, highly selective, and which have a predictable order of elution. The method exhibits increased selectivity for ionic separations particularly for separating anions, as compared to other methods such as IC. During a typical CE separation using the present reagent mixture, cationic iorganic and organic compounds migrate in the opposite direction away from the anions of interest and are not seen in the electropherogram. Neutral and slightly polar impurities are considerably less mobile than the anions and have longer migration times. Thus, the anions of interest are efficiently separated and resolved in the shortest time. The practical usefulness of such increased selectivity can be illustrated, for example, using a fruit juice as the sample. When orange juice is directly injected into an IC system, the first five peaks to elute, which represent fluoride, chloride, nitrite, bromide and nitrate ions, are subjected to interference by carboxylic acids, such as citrate, and other organic compounds in the sample. To reduce this interference, analysis of the anions in the juice using IC would require a complicated pretreatment of the sample to remove the carboxylates and organic compounds. The same sample can be successfully analyzed by CE, and good separation of the anions can be obtained without any pretreatment of the sample using the present method.

The invention is further illustrated by the following Examples.

EXAMPLE 1

General Procedure For CZE of Anions Using $Na_2CrO_4$/TTAB Electrolyte

A sample containing the following eight inorganic anions was prepared: fluoride (F), carbonate ($CO_3$), chloride (Cl), nitrite ($NO_2$), nitrate ($NO_3$), bromide (Br), phosphate ($H_2PO_4$) and sulfate ($SO_2$).

A fused silica capillary externally coated with polyimide (Polymicro Technologies) was freshly cut from a roll and approximately 1 cm section of polyimide coating was burned off with a butane lighter for UV to pass through at 40.5 cm from one end. The total capillary length was 63 cm, and had an internal diameter of 75 $\mu$m. The capillary was installed into the cell and purged with electrolyte with a 1 cc luer syringe with an adapter. The electrolyte was 5 mM $Na_2CrO_4$ and 0.5 mM TTAB, adjusted to pH 8 with 10 mN sulfuric acid. A 50 ml beaker and a 100 ml beaker were filled with electrolyte to equal heights. The 50 ml beaker was placed at the cathode end of the capillary and the 100 ml was placed at the anode end. Approximately 100 microliters of carrier electrolyte was run through the capillary prior to analysis.

The power supply (Spellman (0 to 30 KV)) was manually turned to zero. The capillary at the cathode end was picked up manually, raised to 16 cm height above the electrolyte level and placed in the sample for 30 seconds. The capillary was removed from the sample and placed promptly into the electrolyte. The voltage was manually ramped from 0 to 20 KV during approximately 10 seconds while the start integrate signal was initiated at the beginning of the voltage ramp. At 20 KV a typical current reading was about 20 $\mu$A.

Detection was carried out using a Linear Instruments variable UV/Vis CE detector at two different wavelengths: 254 nm and 272 nm.

Separation was completed in about three minutes, and a clear and distinct peak was obtained for each anion. All eight anions were separated within about one minute.

EXAMPLE 2

CE Separation of a Complex Mixture of Anions

The separation of a complex mixture of ten (10) weakly and strongly dissociated anionic species was carried out according to the procedure described in Example 1. The ten anions in the mixture were Cl, $SO_4$, $NO_3$, F, $CO_3$, formate, acetate, propionate, butyrate and an unidentified organic acid. Separation was completed within about 3.8 minutes. All ten anions eluted and were detected, and a clear and distinct peak was obtained for each anion.

EXAMPLE 3

CE Separation of a Complex Mixture of Nineteen Anions

The separation of a complex mixture of nineteen anionic species was carried out according to the general procedure described in Example 1. The injection volume was 20 nl, and indirect UV/visible detection was carried out at 272 nm. The nineteen anions were:

|     | anion            | ppm |
| --- | ---------------- | --- |
| 1.  | bromide          | 4   |
| 2.  | chloride         | 2   |
| 3.  | sulfate          | 4   |
| 4.  | nitrite          | 4   |
| 5.  | nitrate          | 4   |
| 6.  | molybdate        | 20  |
| 7.  | citrate          | 4   |
| 8.  | fluoride         | 1   |
| 9.  | phosphate        | 4   |
| 10. | phosphite        | 4   |
| 11. | phthalate        | 4   |
| 12. | methanesulfonate | 5   |
| 13. | ethane sulfonate | 5   |
| 14. | acetate          | 5   |
| 15. | propanesulfonate | 5   |
| 16. | butane sulfonate | 5   |
| 17. | benzoate         | 5   |
| 18. | pentane sulfonate| 5   |
| 19. | hexane sulfonate | 5   |

Separation was completed in less than four minutes. All nineteen anions were detected and a clear and distinct peak was obtained for each anion, as shown in FIG. 1. The numbers on the peaks correspond to the numbers in the above list of anions.

EXAMPLE 4

Comparison of a CE Separation and an IC Separation of Fifteen Anions

The separation of a mixture of 15 anions was carried out by CE according to the procedure set out in Example 3. The same mixture was separated by IC according to standard IC conditions. The fifteen anions were

|     | anion              | ppm |
| --- | ------------------ | --- |
| 1.  | thiosulfate        | 4   |
| 2.  | bromide            | 2   |
| 3.  | chloride           | 2   |
| 4.  | sulfate            | 4   |
| 5.  | nitrite            | 4   |
| 6.  | nitrate            | 4   |
| 7.  | molybdate          | 20  |
| 8.  | tungstate          | 20  |
| 9.  | monofluorophosphate| 4   |
| 10. | citrate            | 4   |
| 11. | fluoride           | 1   |
| 12. | phosphate          | 4   |

-continued

| | anion | ppm |
|---|---|---|
| 13. | phosphite | 4 |
| 14. | phthalate | 4 |
| 15. | carbonate | 4 |

Figure 2A:
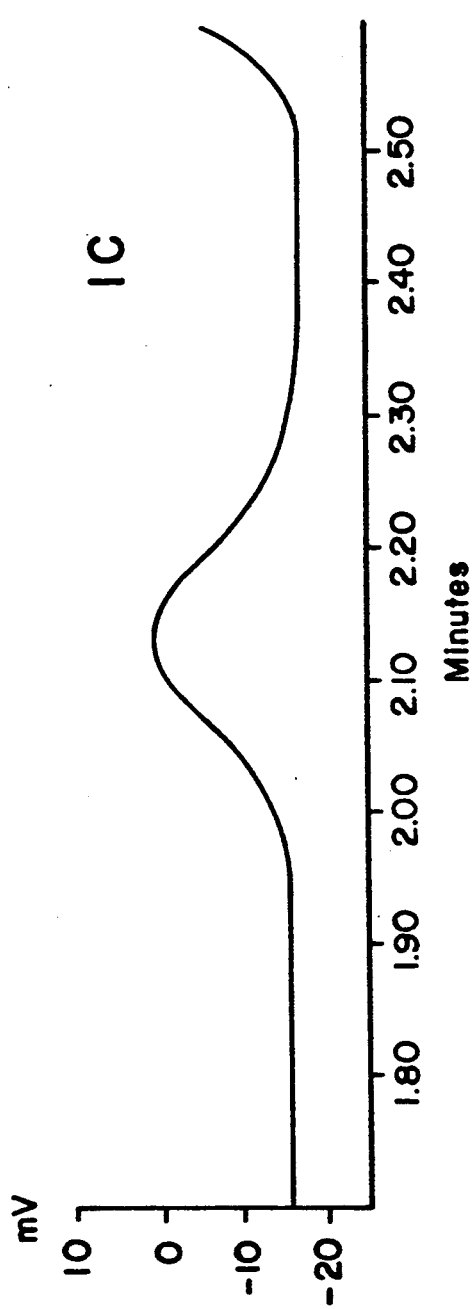
FIG. 2 is a chromatogram showing the separation of fifteen anions by CE using TTAB/Na₂CrO₄ as the carrier electrolyte.

The results are shown in FIG. 2. FIG. 2A is a chromatogram of the IC results after 2.5 minutes. No distinct peaks were obtained. The large rounded peak represents the carbonate ion ($HCO_3^-$), and the curve which starts upward at about the 2.5 minute mark represents the start of the chloride ion ($Cl^-$) peak.

Figure 2B:
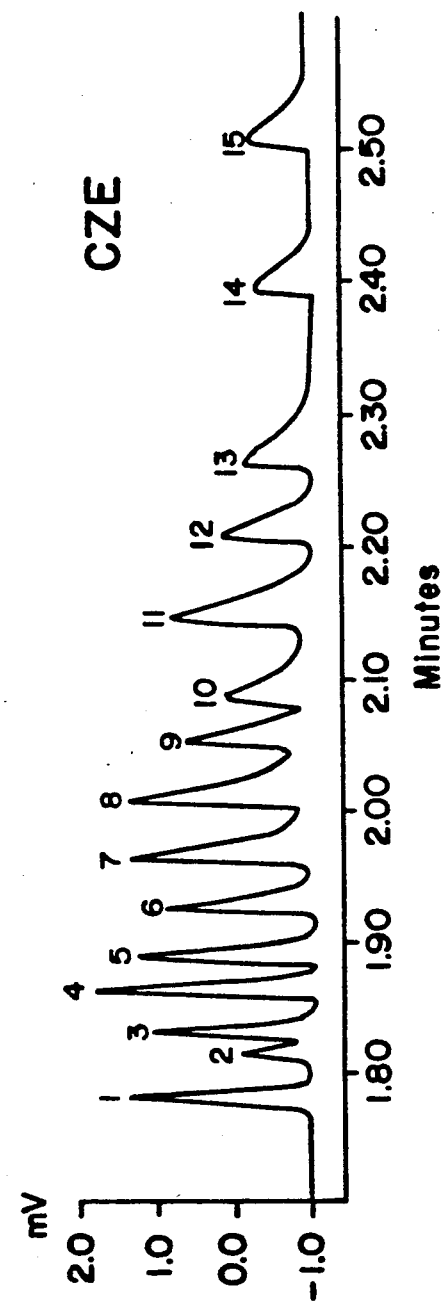

FIG. 2B is a chromatogram showing the CE separation. Separation of all fifteen anions was completed in about 2.5 minutes, and a clear and distinct peak was obtained for each anion.

The results showed that for identical ppm levels of each anion, approximately the same signal to noise ratios were observed by CE from an injection volume of 20 nL as by IC for an injection volume of 100 l. These results indicate that the CE method is about 5000 times more sensitive than conventional IC. In this example, it took about two minutes for an average IC peak to elute under standard conditions wherein the CE method separated fifteen peaks in the same period of time. The observed increase in sensitivity is due to increased separation efficiency: about 1000 theoretical plates for IC vs. about 100,000 for CZE.

EQUIVALENTS

Those skilled in the art will recognize, or be able to ascertain using no more than routine experimentation, equivalents to the specific embodiments of the invention described specifically herein. Such equivalents are intended to be encompassed in the scope of the following claims.

We claim:

1. A method for detecting ions in a sample using capillary zone electrophoresis comprising the steps of:
   a. introducing the sample into a capillary;
   b. immersing the capillary in a mixture containing a chromate salt and an alkyl quaternary ammonium salt;
   c. applying an electrical current under conditions appropriate for the ions in the mixture to move along the capillary toward one of the electrodes thereby causing separation of the ions to occur; and
   d. detecting the ions indirectly using a UV/visible photometric detector.

2. A method of claim 1 wherein the chromate salt is sodium chromate having a concentration of from about 1 mM to about 1.5 nM.

3. A method of claim 1 wherein the alkyl quaternary ammonium salt contains at least one alkyl group having more than four carbon atoms.

4. A method of claim 3 wherein the alkyl quaternary ammonium salt is tetradecyltrimethylammonium bromide having a concentration of from about 0.1 mM to about 1.5 mM.

5. A method of claim 3 wherein the alkyl quaternary ammonium salt is cetyltrimethyl ammonium bromide having a concentration of from about 0.1 mM to about 1.5 mM.

6. A method of claim 1 wherein the alkyl quaternary ammonium salt is immobilized on the capillary wall.

7. A method of claim 1 wherein electrical voltage is from about 5 to about 40 KV.

8. A method of claim 1 wherein the ions are anions.

9. A method of claim 8 wherein the anions are complex organic anions selected from the group consisting of anionic complexes of metals, carboxylic acids, sulfonic acids and alkyl sulfates.

10. A method of claim 8 wherein the anions are inorganic anions.

11. A method for detecting ions in a sample using capillary zone electrophoresis comprising the steps of:
   (a) introducing the sample into a capillary wherein quaternary ammonium salts are bound to the inner capillary wall;
   (b) immersing the capillary in a solution containing a chromate salt;
   (c) applying an electrical current under conditions appropriate for the ions in the solution to move within the capillary toward one of the electrodes thereby causing separation of the ions to occur; and
   (d) detecting the ions indirectly using a UV/visible photometric detector.

* * * * *

UNITED STATES PATENT AND TRADEMARK OFFICE
CERTIFICATE OF CORRECTION

PATENT NO. : 5,104,506
DATED : April 14, 1992
INVENTOR(S) : William R. Jones, Petr Jandik and Michael Merion It is certified that error appears in the above-identified patent and that said Letters Patent is hereby corrected as shown below:

In Claim 2, Column 8, line 9, please change "1.5 nM" to
--- 20 mM ---.

Signed and Sealed this

Twenty-seventh Day of September, 1994

Attest:

BRUCE LEHMAN

Attesting Officer        *Commissioner of Patents and Trademarks*